(12) United States Patent
Little et al.

(10) Patent No.: US 7,507,796 B2
(45) Date of Patent: Mar. 24, 2009

(54) MULTIVALENT ANTIBODY CONSTRUCTS

(75) Inventors: Melvyn Little, Neckargemund (DE); Sergej Kipriyanov, Heidelberg (DE)

(73) Assignee: Deutsches Krehsforschungszentrum Stiftung des Offentlichen Rechts, Heidelberg (DE)

( * ) Notice: Subject to any disclaimer, the term of this patent is extended or adjusted under 35 U.S.C. 154(b) by 0 days.

(21) Appl. No.: 11/546,262

(22) Filed: Oct. 10, 2006

(65) Prior Publication Data
US 2007/0031436 A1   Feb. 8, 2007

Related U.S. Application Data

(63) Continuation of application No. 09/674,794, filed as application No. PCT/DE99/01350 on May 5, 1999, now Pat. No. 7,129,330.

(30) Foreign Application Priority Data
May 5, 1998   (DE) ................ 198 19 846

(51) Int. Cl.
    *C07K 16/00*   (2006.01)
(52) U.S. Cl. .............. 530/387.3; 530/388.22; 424/135.1
(58) Field of Classification Search ............. None
    See application file for complete search history.

(56) References Cited

U.S. PATENT DOCUMENTS

| 5,534,254 | A | 7/1996 | Huston et al. |
| 5,635,599 | A | 6/1997 | Pastan et al. |
| 5,837,242 | A | 11/1998 | Holliger et al. |
| 5,856,456 | A | 1/1999 | Whitlow et al. |
| 5,892,020 | A | 4/1999 | Mezes et al. |
| 6,759,518 | B1 | 7/2004 | Kontermann et al. |
| 2005/0004352 | A1 | 1/2005 | Kontermann et al. |

FOREIGN PATENT DOCUMENTS

EP   0952218 A2   10/1999

OTHER PUBLICATIONS

Holliger et al., 1993. Proc. Natl. Acad. Sci. 90:6444-48.*
Li et al., 1996. The J. Biol. Chem., 26:1817-1820.*
Coloma, et al. Design and production of novel tetravel bispecific antibodies. NatureBiotechnology. 15:159-163, 1997.
Csoka, et al. Activation of T cell cytotoxicity against autologous common acute lymphoblastic leukemia (cALL) blasts by CD3×CD19 bispecific antibody. Leukemia. 1996; 10:1765-1772.
De Jonge, et al. Production and characterization of bispecific single-chain antibody fragments. Molecular Immunology. 1995; 32:1405-1412.
Gruber, et al. Efficient tumor cell lysis mediated by a bispecific single chain antibody expressed in *Escherichia coli*. Journal of Immunology. 1994; 152:5368-5374.
Kipriyanov, et al. Bispecific tandem diabody for tumor therapy with improved antigen binding and pharmacokinetics. Journal of Molecular Biology. 1999; 293:41-56.
Kipriyanov, et al. Rapid detection of recombinant antibody fragments directed against cell-surface antigens by flow cytometry. J. Immunol. Meth. 1996; 196:51-62.
Kipriyanov, et al. Two amino acid mutations in an anti-human CD3 single chain Fv antibody fragment that affect the yield on bacterial secretion but not the affinity. Protein Eng. 1997; 10:445-453.
Kurucz, et al. Retargeting f CTL by an efficiently refolded bispecific single-chain Fv dimer produced in bacteria. Journal of Immunology. 1995; 154:4576-4582.
Mack, et al. A small bispecific antibody construct expressed as a functional single-chain molecule with tumor cell cytotoxicity. Proceedings of the National Academy of Science of the United States. 1995; 92:7021-7025.

* cited by examiner

*Primary Examiner*—Larry R. Helms
*Assistant Examiner*—Meera Natarajan
(74) *Attorney, Agent, or Firm*—Albert P. Halluin; Paul Borchardt; Wilson Sonsini Goodrich & Rosati

(57) ABSTRACT

The present invention relates to a multivalent $F_v$ antibody construct having at least four variable domains which are linked with each over via the peptide linkers 1, 2 and 3. The invention also concerns expression plasmids which code for such an $F_v$ antibody construct and a method of producing the $F_v$ antibody constructs as well as their use.

11 Claims, 10 Drawing Sheets

A
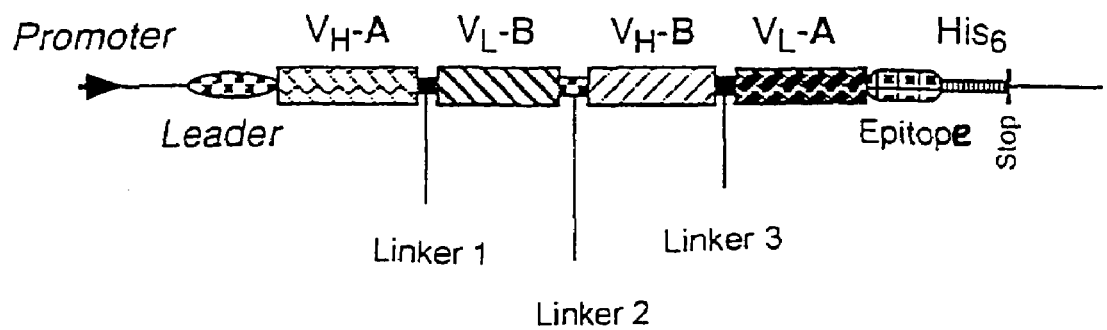
B
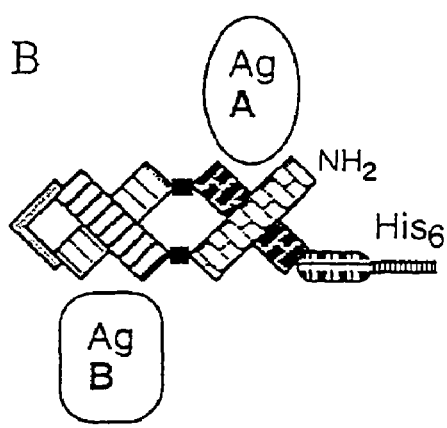
C
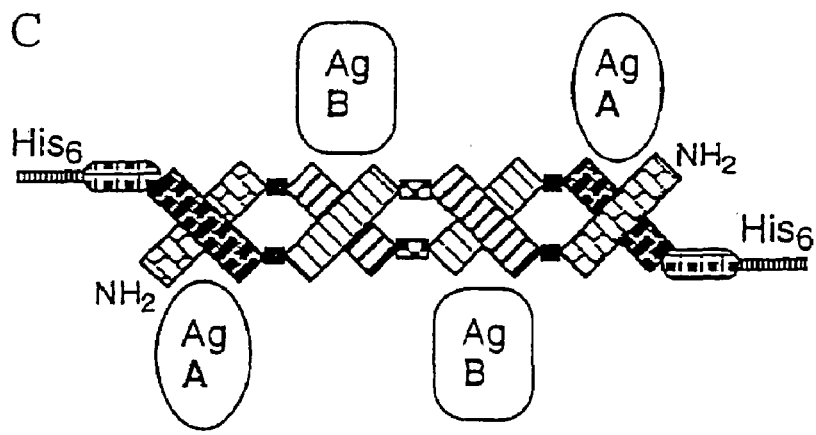
FIGURE 1

```
 941 ATGAGATTTCCTTCAATTTTTACTGCTGTTTTATTCGCAGCATCCTCCGCATTAGCTGCTCCAGTCAACACTAC
   1▶ M  R  F  P  S  I  F  T  A  V  L  F  A  A  S  S  A  L  A  A  P  V  N  T  T
                                    alpha-factor signal
1015 AACAGAAGATGAAACGGCACAAATTCCGGCTGAAGCTGTCATCGGTTACTCAGATTTAGAAGGGGATTTCGATG
  25▶  T  E  D  E  T  A  Q  I  P  A  E  A  V  I  G  Y  S  D  L  E  G  D  F  D 1089 TTGCTGTTTTGCCATTTTCCAACAGCACAAATAACGGGTTATTGTTTATAAATACTACTATTGCCAGCATTGCT
  50▶V  A  V  L  P  F  S  N  S  T  N  N  G  L  L  F  I  N  T  T  I  A  S  I  A
                             Xhol               EcoRI
1163 GCTAAAGAAGAAGGGGTATCTCTCGAGAAAAGAGAGGCTGAAGCTGAATTCCAGGTGCAACTGCAGCAGTC
  75▶ A  K  E  E  G  V  S  L  E  K  R  E  A  E  A  E  F  Q  V  Q  L  Q  Q  S
         VH anti-CD3
1234 TGGGGCTGAACTGGCAAGACCTGGGGCCTCAGTGAAGATGTCCTGCAAGGCTTCT
  98▶  G  A  E  L  A  R  P  G  A  S  V  K  M  S  C  K  A  S
```

FIGURE 7

```
941  ATGAGATTTCCTTCAATTTTTACTGCTGTTTTATTCGCAGCATCCTCCGCATTAGCTGCTCCAGTCAACACTAC
  1) M  R  F  P  S  I  F  T  A  V  L  F  A  A  S  S  A  L  A  A  P  V  N  T  T
                                 alpha-factor signal
1015 AACAGAAGATGAAACGGCACAAATTCCGGCTGAAGCTGTCATCGGTTACTCAGATTTAGAAGGGGATTTCGATG
 25) T  E  D  E  T  A  Q  I  P  A  E  A  V  I  G  Y  S  D  L  E  G  D  F  D
                                                                          BsrDI
1089 TTGCTGTTTTGCCATTTTCCAACAGCACAAATAACGGGTTATTGTTTATAAATACTACTATTGCCAGCATTGCT
 50) V  A  V  L  P  F  S  N  S  T  N  N  G  L  L  F  I  N  T  T  I  A  S  I  A
                       XhoI                      EcoRI
1163 GCTAAAGAAGAAGGGGTATCTCTCGAGAAAAGAGAGGCTGAAGCTGAATTCATGGCGCAGGTGCAACTGCAG
 75) A  K  E  E  G  V  S  L  E  K  R  E  A  E  A  E  F  M  A  Q  V  Q  L  Q
           VH anti-CD3
1235 CAGTCTGGGGCTGAACTGGCAAGACCTGGGGCCTCAGTGAAGATGTCCTGCAAGGCTTCT
 99) Q  S  G  A  E  L  A  R  P  G  A  S  V  K  M  S  C  K  A  S
```

FIGURE 8

MULTIVALENT ANTIBODY CONSTRUCTS

CROSS-REFERENCE

This application is a continuation application of Ser. No. 09/674,794, filed Aug. 21, 2001, now U.S. Pat. No. 7,129,330, issued on Oct. 31, 2006, which is a national phase filing of Application No. PCT/DE99/01350, which was filed with the Patent Cooperation Treaty on May 5, 1999, and is entitled to priority of the German Patent Application 198 19 846.9, filed May 5, 1998, which applications are incorporated herein by reference.

FIELD OF THE INVENTION

The present invention relates to multi-valent $F_v$ antibody constructs, expression plasmids which code for them, and a method for producing the $F_v$ antibody constructs as well as the use thereof.

BACKGROUND OF THE INVENTION

Natural antibodies are dimers and are therefore referred to as bivalent. They have four variable domains, namely two $V_H$ domains and two $V_L$ domains. The variable domains serve as binding sites for an antigen, a binding site being formed from a $V_H$ domain and a $V_L$ domain. Natural antibodies recognize one antigen each, so that they are also referred to as monospecific. Furthermore, they also have constant domains which add to the stability of the natural antibodies. On the other hand, they are also co-responsible for undesired immune responses which result when natural antibodies of various animal species are administered mutually.

In order to avoid such immune responses, antibodies are constructed which lack the constant domains. In particular, these are antibodies which only comprise the variable domains. Such antibodies are designated $F_v$ antibody constructs. They are often available in the form of single-chain monomers paired with one another.

However, it showed that $F_v$ antibody constructs only have little stability. Therefore, their usability for therapeutic purposes is strongly limited.

Thus, it is the object of the present invention to provide an antibody by means of which undesired immune responses can be avoided. Furthermore, it shall have a stability which makes it usable for therapeutic uses.

According to the invention this is achieved by the subject matters defined in the claims.

SUMMARY OF THE INVENTION

The present invention relates to a multivalent a multi-valent $F_v$ antibody construct having at least four variable domains which are linked with each other via the peptide linkers 1, 2 and 3. The invention also concerns expression plasmids which code for an $F_v$ antibody construct and a method of producing the $F_v$ antibody constructs as well as their use.

BRIEF DESCRIPTION OF THE DRAWINGS

FIG. 1 shows the genetic organization of an $F_v$ antibody construct (A) according to the invention and schemes for forming a bivalent (B) or tetravalent $F_v$ antibody construct (C) Ag: antigen; $His_6$: six C-terminal histidine residues; stop: stop codon (TAA); $V_H$ and $V_L$: variable region of the heavy and light chains.

FIG. 5 shows the nucleotide sequence and the amino acid sequence derived therefrom of the bivalent $F_v$ antibody construct encoded by the expression plasmid pDIS3x19-LL. c-myc epitope: sequence coding for an epitope which is recognized by the antibody 9E10; CDR: region determining the complementarity; framework: framework region; His6 tail: sequence which codes for six C-terminal histidine residues; PelB leader: signal peptide sequence of the bacterial pectate lyase; RBS: ribosome binding site; $V_H$ and $V_L$: variable region of the heavy and light chains.

FIG. 6 shows the nucleotide sequence and the derived amino acid sequence of the tetravalent $F_v$ antibody construct encoded by the expression plasmid pDISC3x19-SL. c-myc epitope: sequence coding for an epitope which is recognized by the 9E10 antibody; CDR: region determining complementarity; framework: framework region; His6 tail: sequence coding for the six C-terminal histidine residues; PelB leader: signal peptide sequence of the bacterial pectate lyase; RBS: ribosome binding site; $V_H$ and $V_L$: variable region of the heavy and light chains.

FIG. 7 shows the nucleotide sequence and the derived amino acid sequence of a connection between a gene which codes for an α-factor leader sequence and a gene coding for the tetravalent $F_v$ antibody construct in the *Pichia* expression plasmid pPIC-DISC-SL. Alpha-factor signal: leader peptide sequence of the *Saccharomyces cerevisiae*-α factor secretion signal; $V_H$: variable region of the heavy chain. Rhombs indicate the signal cleaving sites.

FIG. 8 shows the nucleotide sequence and the derived amino acid sequence of a connection between a gene coding for an α-factor leader sequence and a gene which codes for the bivalent $F_v$ antibody construct in the *Pichia* expression plasmid pPIC-DISC-LL. Alpha-factor signal: leader peptide sequence of the *Saccharomyces cerevisiae*-α-factor secretion signal; $V_H$: variable region of the heavy chain. Rhombs show the signal cleaving sites.

DETAILED DESCRIPTION OF THE INVENTION

Figure 2:
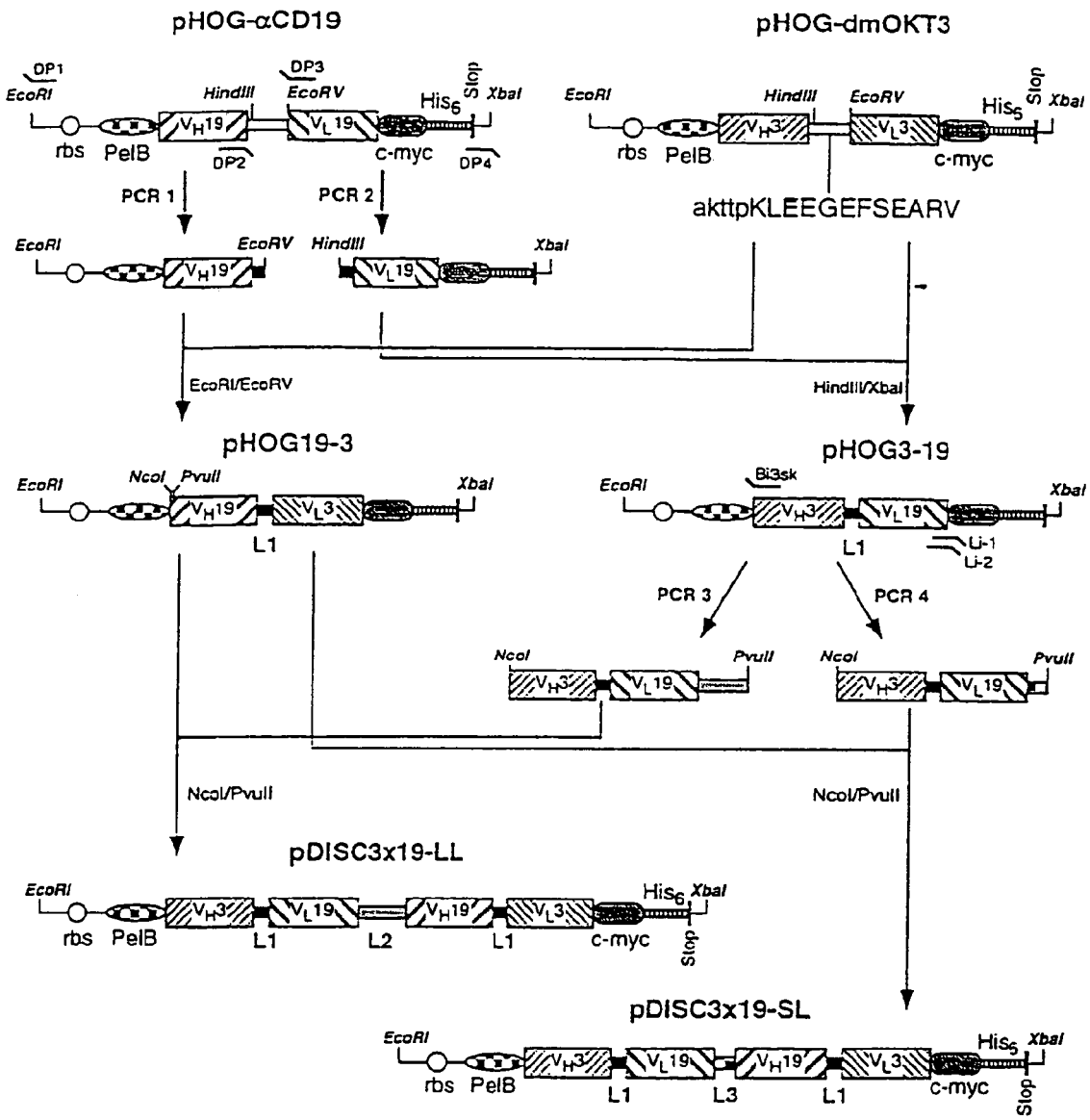
FIG. 2 shows the scheme for the construction of the plasmids pDISC3x19-LL and pDISC3x19-SL. c-myc: sequence coding for an epitope which is recognized by the antibody 9E1, $His_6$: sequence which codes for six C-terminal histidine residues; PelB: signal peptide sequence of the bacterial pectate lyase (PelB leader); rbs: ribosome binding site; Stop: stop codon (TAA); $V_H$ and $V_L$: variable region of the heavy and light chains.

It is the object of the present invention to provide an antibody by means of which undesired immune responses can be avoided. Furthermore, it shall have a stability which makes it useable for therapeutic use.

Therefore, the subject matter of the present invention relates to a multi-valent $F_v$ antibody construct which has great stability. Such a construct is suitable for diagnostic and therapeutic purposes.

The present invention is based on the applicant's insights that the stability of an $F_v$ antibody construct can be increased if it is present in the form of a single-chain dimer where the four variable domains are linked with one another via three peptide linkers. The applicant also recognized that the $F_v$ antibody construct folds with itself when the middle peptide linker has a length of about 10 to 30 amino acids. The applicant also recognized that the $F_v$ antibody construct folds with other $F_v$ antibody constructs when the middle peptide linker has a length of about up to 10 amino acids so as to obtain a multimeric, i.e. multi-valent, $F_v$ antibody construct. The applicant also realized that the $F_v$ antibody construct can be multi-specific.

According to the invention the applicant's insights are utilized to provide a multi-valent $F_v$ antibody construct which comprises at least four variable domains which are linked with one another via peptide linkers 1, 2 and 3.

The expression "$F_v$ antibody construct" refers to an antibody which has variable domains but no constant domains.

The expression "multivalent $F_v$ antibody construct" refers to an $F_v$ antibody which has several, but at least four, variable domains. This is achieved when the single-chain $F_v$ antibody construct folds with itself so as to give four variable domains, or folds with other single-chain $F_v$ antibody constructs. In the latter case, an $F_v$ antibody construct is given which has 8, 12, 16, etc., variable domains. It is favorable for the $F_v$ antibody construct to have four or eight variable domains, i.e. it is bivalent or tetravalent (FIG. 1). Furthermore, the variable domains may be equal or differ from one another, so that the antibody construct recognizes one or several antigens. The antibody construct preferably recognizes one or two antigens, i.e. it is monospecific and bispecific, respectively. Examples of such antigens are proteins CD19 and CD3.

The expression "peptide linkers 1, 3" refers to a peptide linker adapted to link variable domains of an $F_v$ antibody construct with one another. The peptide linker may contain any amino acids, the amino acids glycine (G), serine (S) and proline (P) being preferred. The peptide linkers 1 and 3 may be equal or differ from each other. Furthermore, the peptide linker may have a length of about 0 to 10 amino acids. In the former case, the peptide linker is only a peptide bond from the COOH residue of one of the variable domains and the $NH_2$ residue of another of the variable domains. The peptide linker preferably comprises the amino acid sequence GG.

The expression "peptide linker 2" refers to a peptide linker adapted to link variable domains of an $F_v$ antibody construct with one another. The peptide linker may contain any amino acids, the amino acids glycine (G), serine (S) and proline (P) being preferred. The peptide linker may also have a length of about 3 to 10 amino acids, in partiuclar 5 amino acids, and most particularly the amino acid sequence GGPGS, which serves for achieving that the single-chain $F_v$ antibody construct folds with other single-chain $F_v$ antibody constructs. The peptide linker can also have a length of about 11 to 20 amino acids, in particular 15 to 20 amino acids, and most particularly the amino acid sequence $(G_4S)_4$, (SEQ ID NO:14) which serves for achieving that the single-chain $F_v$ antibody construct folds with itself.

An $F_v$ antibody construct according to the invention can be produced by common methods. A method is favorable in which DNAs coding for the peptide linkers 1, 2 and 3 are ligated with DNAs coding for the four variable domains of an $F_v$ antibody construct such that the peptide linkers link the variable domains with one another and the resulting DNA molecule is expressed in an expression plasmid. Reference is made to Examples 1 to 6. As to the expressions "$F_v$ antibody construct" and "peptide linker" reference is made to the above explanations and, by way of supplement, to Maniatis, T. et al., *Molecular Cloning, A Laboratory Manual*, Cold Spring Harbor Laboratory 1982.

DNAs which code for an $F_v$ antibody construct according to the invention also represent a subject matter of the present invention. Furthermore, expression plasmids which contain such DNAs also represent a subject matter of the present invention. Preferred expression plasmids are pDISC3x19-LL, pDISC3x19-SL, pPIC-DISC-LL, pPIC-DISC-SL, pDISC5-LL and pDISC6-SL. The first four were deposited with the DSMZ (Deutsche Sammlungfur Mikroorganismen und Zellen) [German-type collection for micro-organisms and cells] on Apr. 30, 1998 under DSM 12150, DSM 12149, DSM 12152 and DSM 12151, respectively.

Another subject matter of the present invention relates to a kit, comprising:
(a) an $F_v$ antibody construct according to the invention, and/or
(b) an expression plasmid according to the invention, and
(c) conventional auxiliary agents, such as buffers, solvents and controls.

One or several representatives of the individual components may be present.

The present invention provides a multi-valent $F_v$ antibody construct where the variable domains are linked with one another via peptide linkers. Such an antibody construct distinguishes itself in that it contains no parts which can lead to undesired immune reactions. Furthermore, it has great stability. It also enables to bind several antigens simultaneously. Therefore, the $F_v$ antibody construct according to the invention is perfectly adapted to be used not only for diagnostic but also for therapeutic purposes. Such purposes can be seen as regards any disease, in particular a viral, bacterial or tumoral disease.

The invention is explained by the below examples. The following preparations and examples are given to enable those skilled in the art to more clearly understand and to practice the present invention. The present invention, however, is not limited in scope by the exemplified embodiments, which are intended as illustrations of single aspects of the invention only, and the methods which are functionally equivalent are within the scope of the invention. Indeed, various modifications of the invention in addition to those described herein will become apparent to those skilled in the art from the foregoing description and accompanying drawings. Such modification are intended to fall within the scope of the appended claims.

EXAMPLES

Example 1

Figure 3:
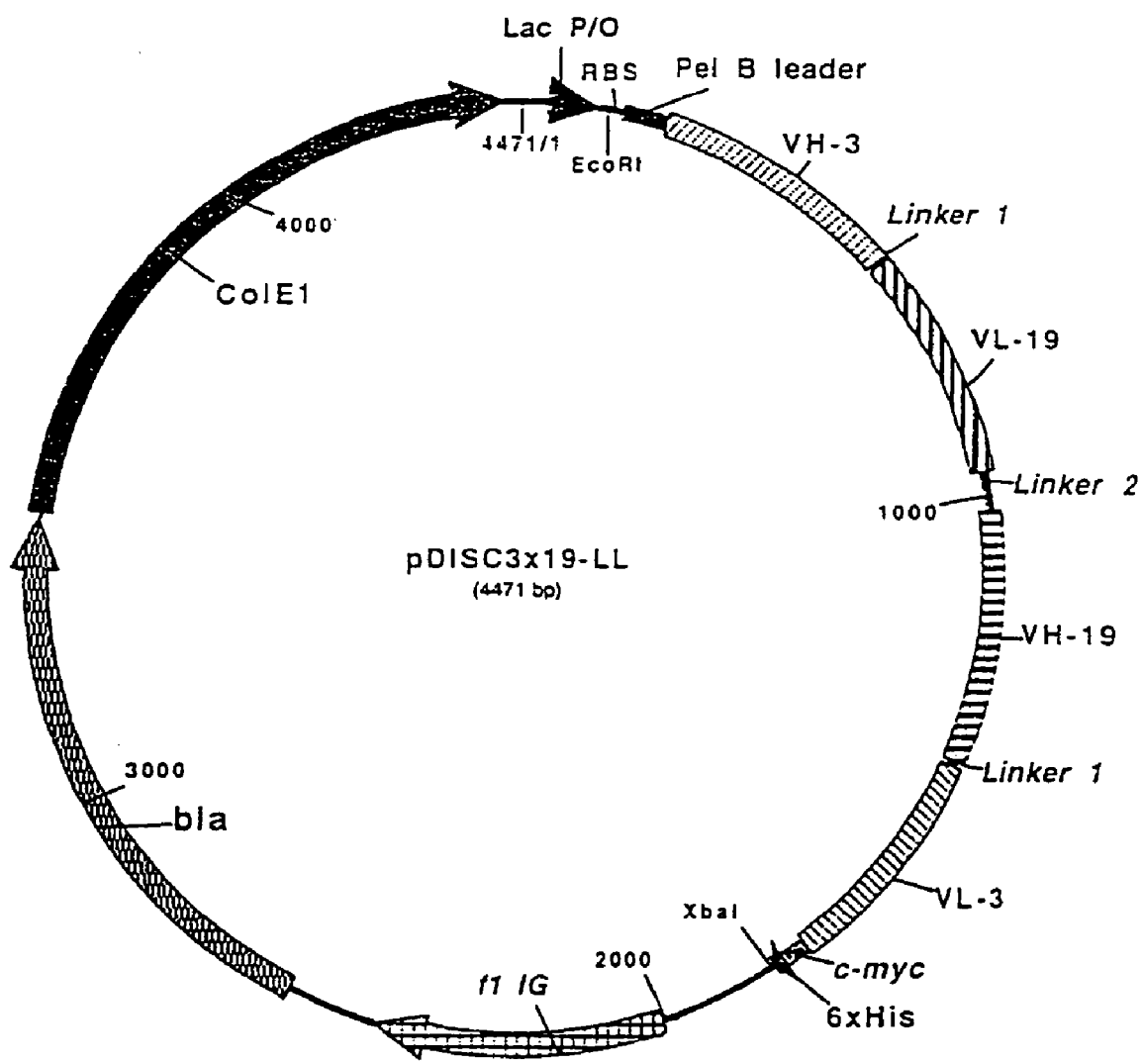
FIG. 3 shows a diagram of the expression plasmid pDISC3x19-LL. 6×His: sequence which codes for six C-terminal histidine residues; bla: gene which codes for β-lactamase responsible for ampicillin resistance; bp: base pairs; c-myc: sequence coding for an epitope which is recognized by the 9E10antibody; ColE1: origin of the DNA replication; f1-IG: intergenic region of the bacteriophage f1; Lac P/O: wt lac-operon promoter/operator; linker 1: sequence which codes for a GlyGly dipeptide linking the $V_H$ and $V_L$ domains; linker 2: sequence coding for a $(Gly_4Ser)_4$ polypeptide which links the hybrid scFv fragments; Pel-B leader: signal peptide sequence of the bacterial pectate lyase; rbs: ribosome binding site; $V_H$ and $V_L$: variable region of the heavy and light chains.
Figure 4:
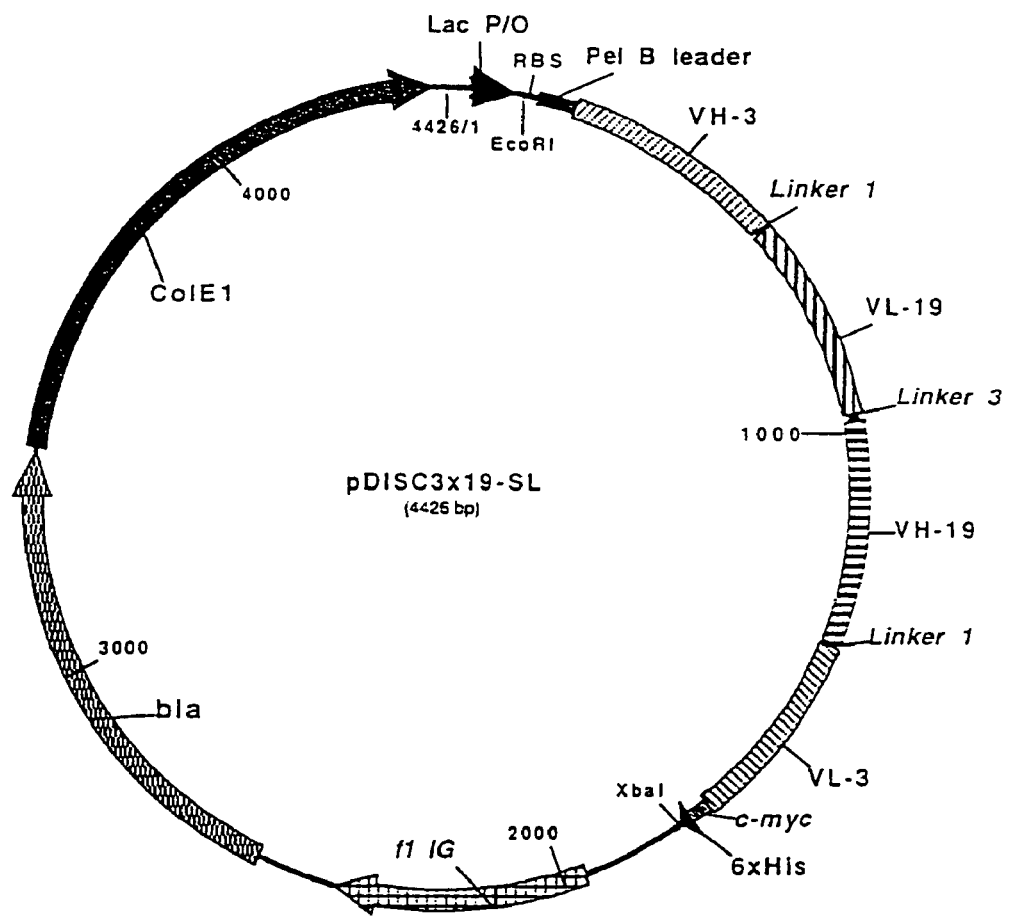
FIG. 4 shows a diagram of the expression plasmid pDISC3x19-SL. 6×His: sequence which codes for six C-terminal histidine residues; bla: gene which codes for β-lactamase which is responsible for the ampicillin resistance; bp: base pairs; c-myc: sequence coding for an epitope recognized by the 9E10 antibody; ColE1: origin of DNA replication; f1-IG: intergenic region of the bacteriophage f1; Lac P/O: wt lac-operon promoter/operator: linker 1: sequence which codes for a GlyGly dipeptide which links the $V_H$ and $V_L$ domains; linker 3: sequence which codes for a GlyGlyProGlySer oligopeptide which links the hybrid scFv fragments; Pel-B leader: signal peptide sequence of the bacterial pectate lyase; rbs: ribosome binding site; $V_H$ and $V_L$: variable region of the heavy and light chains.
Figure 5:
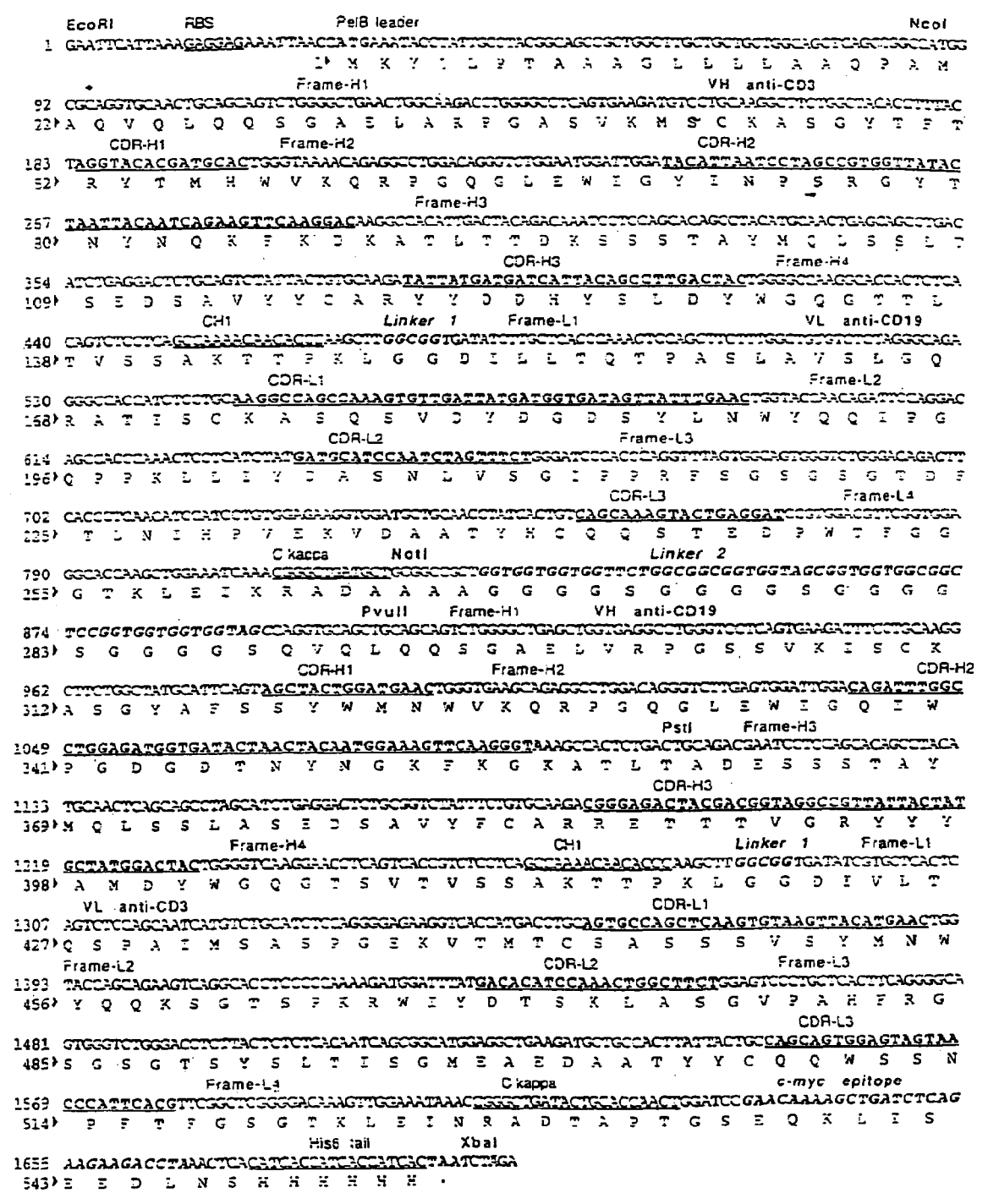
Figure 6:
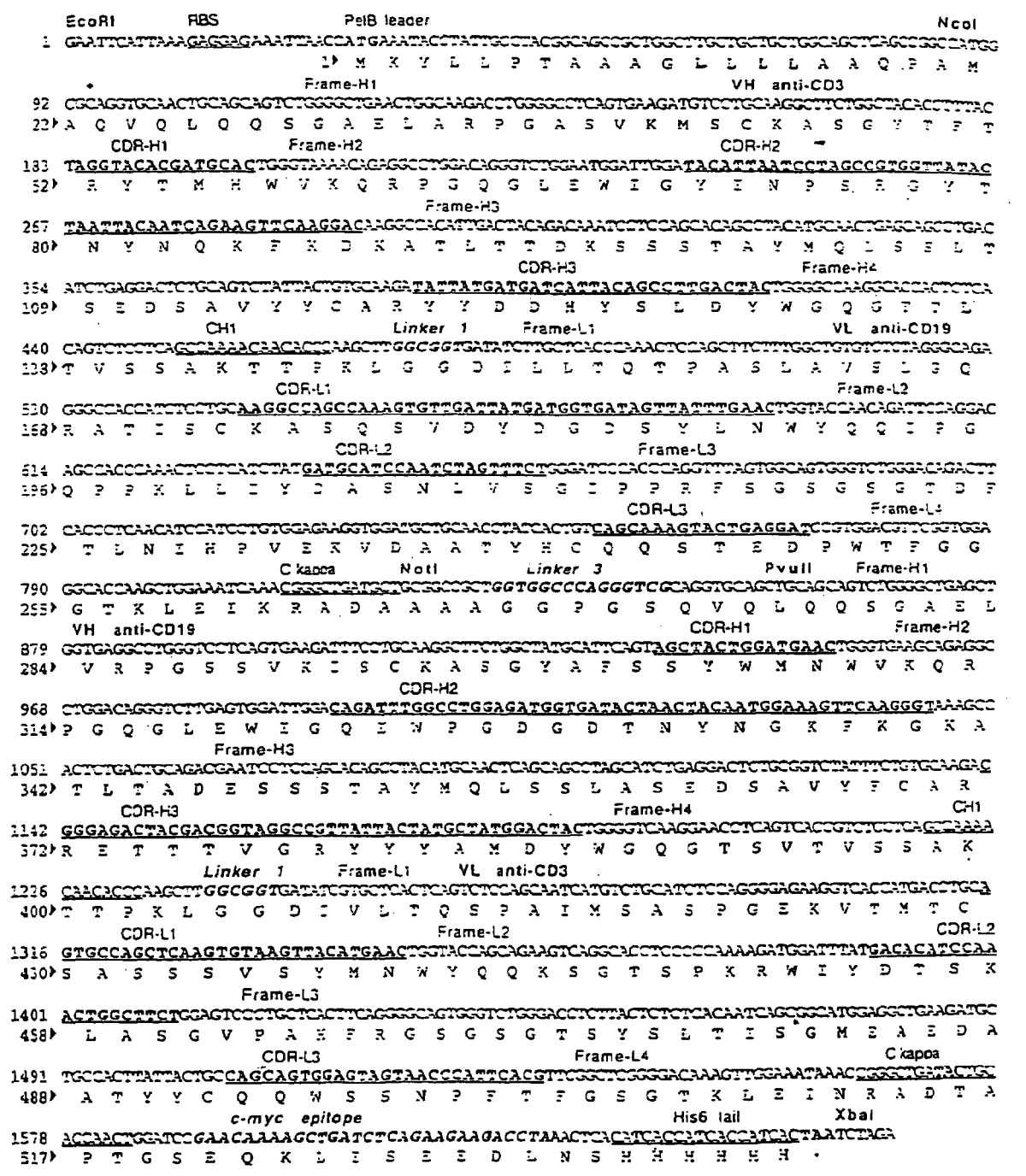

Construction of the Plasmids pDISC3x19-LL and pDISC3x19-SL for the Expression of Bivalent, Bispecific and/or Tetravalent, Bispecific $F_v$ Antibody Constructs in Bacteria The plasmids pHOG-αCD19 and pHOG-dmOKT3 which code for the scFv fragments derived from the hybridoma HD37 which is specific to human CD19 (Kipriyanov et al., 1996, J. Immunol. Meth. 196, 51-62) and from the hybridoma OKT3 which is specific to human CDS (Kipriyanov et al., 1997, Protein Eng. 10, 445-453), respectively, were used for the construction of expression plasmids for a single-chain $F_v$ antibody construct. A PCR fragment 1 of the $V_H$ domain of anti-CD19, followed by a segment which codes for a GlyGly linker, was produced using the primers DP1,5'-TCACACA GAATTC-TTAGATCTATTAAAGAGGAGAAATTAACC (SEQ ID NO:1) and DP2,5-AGCACAC GATATCACCGCCAAGCTTGGGTGTTGTTTTGGC (SEQ ID NO:2)(FIG. 2). The PCR fragment 1 was cleaved by EcoRI and EcoRV and ligated with the EcoRI/EcoRV-linearized plasmid pHOG-dmOKT3 so as to produce the vector pHOG19-3. The PCR fragment 2 of the $V_L$ domain of anti-CD19, followed by a segment which codes for a c-myc epitope and a hexahistidinyl tail, was produced using the primers DP5, 5'-AGCACACAAGCTTGG CGGT-GATATCTTGCTCACCCAAACTCCA (SEQ ID NO:3) and DP4, 5'-AGCACACTCTAGAGACACACAGATCTTT AGTGATGGTGATGGTGATGTG AGTTTAGG (SEQ ID NO:4). The PCR fragment 2 was cleaved by HindIII and XbaI and ligated with the HIndIII/XbaI-linearized plasmid pHOG-dmOKT3 so as to obtain the vector pHOG3-19 (FIG. 2). The gene coding for the hybrid scFv-3-19 in the plasmid pHOG3-19 was amplified by means of PCR with the primers Bi3sk, 5'-CAGCCGGCCATGGCGCAGGTGCAACTGCAGCAG (SEQ ID NO:5) and either Li-1,5'-TATATACTG CAGCTGCACCTGGCTACCACCACCACCGGAGCCG CCACCACCGCTACCACCGCCGCCAG AACCACCAC-CACCAGCGGCCGCAGCATCAGCCCG (SEQ ID NO:6) for the production of a long flexible (Gly$_4$Ser)$_4$ inter-scFV linker (PCR fragment 3, FIG. 2) or Li-2,5'-TATATACTG CAGCTGCACCTGCGACCCTGGGCCACCAGCGGCC GCAGCATCAGCCCG (SEQ ID NO:7), for the production of a short rigid GGPGS linker (PCR fragment 4, FIG. 2). The expression plasmids pDISC3x19-LL and pDISC3x19-SL were constructed by ligating the NcoI/PvuII restriction fragment from pHOG19-3, comprising the vector framework and the NcoI/PvuII-cleaved PCR fragments 3 and 4, respectively (FIGS. 3, 4). The complete nucleotide and protein sequences of the bivalent and tetravalent $F_v$ antibody constructs are indicated in FIGS. 5 and 6, respectively.

Example 2

Construction of the Plasmids pPIC-DISC-LL and pPIC-DISC-SL for the Expression of Bivalent, Bispecific and/or Tetravalent, Bispecific $F_v$ Antibody Constructs in Yeast (A) Construction of pPIC-DISC-SL.

The vector pPICZαA (Invitrogen BV, Leek, Netherlands) for the expression and secretion of recombinant proteins in the yeast *Pichia pastoris* was used as a starting material. It contains a gene which codes for the *Saccharomyces cerevisiae* α-factor secretion signal, followed by a polylinker. The secretion of this vector is based on the dominant selectable marker, Zeocin™ which is bifunctional in both *Pichia* and *E. coli*. The gene which codes for the tetravalent $F_v$ antibody construct (scDia-SL) was amplified by means of PCR by the template pDISC3x19-SL using the primers 5-PIC, 5'-CCGT GAATTCCAGGTGCAACTGCAGCAGTCTGGGGCTG AACTGGC and pSEXBn (SEQ ID NO:8). 5'-GGTC-GACGTTAACCGACAAACAACAGATAAAACG (SEQ ID NO:9). The resulting PCR product was cleaved by EcoRI and XbaI and ligated in EcoRI/XbaI-linearized pPICZαA. The expression plasmid pPIC-DISC-SL was obtained. The nucleotide and protein sequences of the tetravalent $F_v$ antibody construct are shown in FIG. 7.

(B) Construction of pPIC-DISC-LL.

The construction of pPIC-DISC-LL was carried out on the basis of pPICZαA (Invitrogen-BV, Leek, Netherlands) and pDISC3x19-LL (FIG. 3). The plasmid-DNA pPICZαA was cleaved by EcoRI. The overhanging 5'-ends were filled using a Klenow fragment of the *E. coli* DNA polymerase I. The resulting DNA was cleaved by XbaI, and the large fragment comprising the pPIC vector was isolated. Analogous thereto the DNA of pDISC3x19-LL was cleaved by NcoI and treated with a Klenow fragment. Following the cleavage using XbaI a small fragment, comprising a gene coding for the bivalent $F_v$ antibody, was isolated. Its ligation with a pPIC-derived vector-DNA resulted in the plasmid pPIC-DISC-LL. The nucleotide and protein sequences of the bivalent $F_v$ antibody construct are shown in FIG. 8.

Example 3

Expression of the Tetravalent and/or Bivalent $F_v$ Antibody Construct in Bacteria E. coli XLI-blue cells (Strategene, La Jolla, Calif.) which had been transformed with the expression plasmids pDISC3x19-LL and pDISC3x19-SL, respectively, were cultured overnight in 2×YT medium with 50/µg/ml ampicillin and 100 mM glucose (2×YT$_{Ga}$) at 37° C. 1:50 dilutions of the overnight cultures in 2×YT$_{GA}$ were cultured as flask cultures at 37° C. while shaking with 200 rpm. When the cultures had reached an OD$_{600}$ value of 0.8, the bacteria were pelleted by 10-minute centrifugation with 1500 g at 20° C. and resuspended in the same volume of a fresh 2×YT medium containing 50 µg/ml ampicillin and 0.4 M saccharose. IPTG was added up to a final concentration of 0.1 mM, and the growth was continued at room temperature (20-22° C.) for 18-20 h. The cells were harvested by 10-minute centrifugation with 5000 g at 4° C. The culture supernatant was held back and stored on ice. In order to isolate the soluble periplasmic proteins, the pelleted bacteria were resuspended in 5% of the initial volume of ice-cold 50 mM Tris-HCl, 20% saccharose, 1 mM EDTA, pH 8.0. Following 1 hour of incubation on ice with occasional stirring the spheroplasts were centrifuged with 30,000 g at 4° C. for 30 minutes, the soluble periplasmic extract being obtained as supernatant and the spheroplasts with the insoluble periplasmic material being obtained as pellet. The culture supernatant and the soluble periplasmic extract were combined and clarified by further centrifugation (30,000 g, 4° C., 40 min.). The recombinant product was concentrated by ammonium sulfate precipitation (final concentration 70% saturation). The protein precipitate was obtained by centrifugation (10,000 g, 4° C., 40 min.) and dissolved in 10% of the initial volume of 50 mM Tris-HCl, 1 M NaCl, pH 7.0. An immobilized metal affinity chromatography (IMAC) was carried out at 4° C. using a 5 ml column of chelating sepharose (Pharmacia) which was charged with $Cu^{2+}$ and had been equilibrated with 50 mM Tris-HCl, 1 M NaCl, pH 7.0 (starting buffer). The sample was loaded by passing it over the column. It was then washed with twenty column volumes of starting buffer, followed by starting buffer with 50 mM imidazole until the absorption at 280 nm of the effluent was at a minimum (about thirty column volumes). The absorbed material was eluted with 50 mM Tris-HCl, 1 M NaCl, 250 mM imidazole, pH 7.0.

The protein concentrations were determined with the Bradford dye binding test (1976, Anal. Biochem. 72, 248-254) using the Bio-Rad (Munich, Germany) protein assay kit. The concentrations of the purified tetravalent and bivalent $F_v$ antibody constructs were determined from the $A_{280}$ values using the extinction coefficients $\epsilon^{1\ mg/ml}$=1.96 and 1.93, respectively.

Example 4

Expression of the Tetravalent and/or Bivalent Antibody Construct in the Yeast *Pichia pastoris*

Competent *P. pastoris* GS155 cells (Invitrogen) were electroporated in the presence of 10 µg plasmid-DNA of pPIC-DISC-LL and pPIC-DISC-SL, respectively, which had been linearized with SacI. The transformants were selected for 3 days at 30° C. on YPD plates containing 100 µg/ml Zeocin™. The clones which secreted the bivalent and/or tetravalent $F_v$ antibody constructs were selected by plate screening using an anti-c-myc-mAk 9E10 (1C Chemikalien, Ismaning, Germany).

For the expression of the bivalent $F_v$ antibody constructs and tetravalent $F_v$ antibody constructs, respectively, the clones were cultured in YPD medium in shaking flasks for 2 days at 30° C. with stirring. The cells were centrifuged resuspended in the same volume of the medium containing methanol and incubated for another 3 days at 30° C. with stirring. The supernatants were obtained after the centrifugation. The recombinant product was isolated by ammonium sulfate precipitation, followed by IMAC as described above.

Example 5

Characterization of the Tetravalent $F_v$ Antibody Construct and Bivalent $F_v$ Antibody Construct, Respectively (A) Size Exclusion Chromatography.

An analytical gel filtration of the $F_v$ antibody constructs was carried out in PBS using a superdex 200-HR10/30 column (Pharmacia). The sample volume and the flow rate were 200 µl/min and 0.5 ml/min, respectively. The column was calibrated with high-molecular and low-molecular gel filtration calibration kits (Pharrmacia).

(B) Flow Cytometry.

The human CD3$^+$/CD19$^-$-acute T-cell leukemia line Jurkat and the CD19$^+$/CD3$^-$B-cell line JOK-1 were used for flow cytometrie. 5×10$^5$ cells in 50 µl RPMI 1640 medium (GIBCO BRL, Eggestein, Germany) which was supplemented with 10% PCS and 0.1% sodium azide (referred to as complete medium) were incubated with 100 µl of the $F_v$ antibody preparations for 45 minutes on ice. After washing using the complete medium the cells were incubated with 100 µl 10 µg/ml anti-cmyc-Mak 9E10 (1C Chemikalien) in the same buffer for 45 minon ice. After a second wash cycle, the cells were incubated with 100 µl of the FITC-labeled goat-anti-mouse-IgG (GIBCO BRL) under the same conditions as before. The cells were then washed again and resuspended in 100 µl 1 µg/ml propidium iodide solution (Sigma, Deisenhofen, Germany) in complete medium with the exclusion of dead cells. The relative fluorescence of the stained cells was measured using a FACScan flow cytometer (Becton Dickinson, Mountain View, Calif.).

(C) Cytotoxicity Test.

The GDI9-expressing Burkitt lymphoma cell line Raji and Namalwa were used as target cells. The cells were incubated in RPMI 1640 (GIBCO BRL) which was supplemented with 10% heat-inactivated PCS (GIBCO BRL), 2 mM glutamine and 1 mM pyruvate, at 37° C. in a dampened atmosphere with 7.5% CO$_2$. The cytotoxic T-cell tests were carried out in RPMI-1640 medium supplemented with 10% FCS, 10 mM HEPES, 2 mM glutamine, 1 mM pyruvate and 0.05 mM 2-ME. The cytotoxic activity was evaluated using a standard [$^{51}$Cr] release test; 2×10$^6$ target cells were labeled with 200 µCi Na [$^{51}$Cr] O$_4$ (Amersham-Buchler, Braunschweig, Germany) and washed 4 times and then resuspended in medium in a concentration of 2×10$^5$/ml. The effector cells were adjusted to a concentration of 5×10$^6$/ml. Increasing amounts of CTLs in 100 µl were titrated to 10$^4$ target cells/well or cavity in 50 µl. 50 µl antibodies were added to each well. The entire test was prepared three times and incubated at 37° C. for 4 h. 100 µl of the supernatant were collected and tested for [$^{51}$Cr] release in a gamma counter (Cobra Auto Gamma;

Canberra Packard, Dreieich, Germany). The maximum release was determined by incubation of the target cells in 10% SDS, and the spontaneous release was determined by incubation of the cells in medium alone. The specific lysis (%) was calculated as: (experimental release−spontaneous release)/(maximum release−spontaneous release)×100.

Example 6

Figure 9:
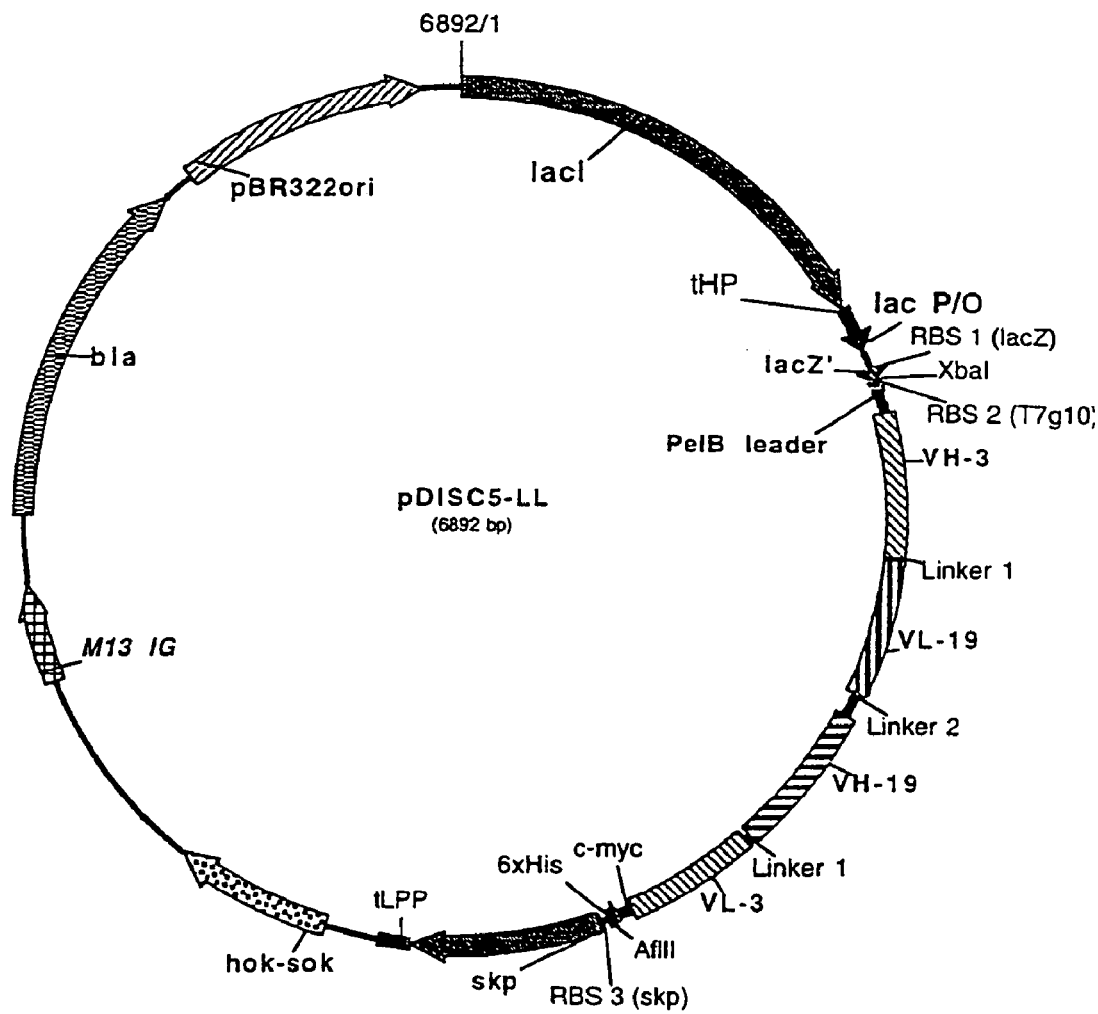
FIG. 9 shows a diagram of the expression plasmid pDISC5-LL. 6×His: sequence coding for six C-terminal histidine residues; bla: gene which codes for β-lactamase responsible for ampicillin resistance; bp: base pairs; c-myc: sequence coding for an epitope which is recognized by the 9E10 antibody; hok-sok: plasmid-stabilizing DNA locus; Lacd: gene which codes for the Lac represser; Lac P/O: wt lac-operon-promoter/operator, LacZ': gene which codes for the α-peptide of β-galactosidase, linker 1: sequence which codes for a GlyGly dipeptide connecting the $V_H$ and $V_L$ domains; linker 2: sequence which codes for a $(Gly_4Ser)_4$ polypeptide linking the hybrid scFv fragments; M13 IG: intergenic region of the M13 bacteriophage; pBR322ori: origin of DNA replication; Pel-B leader: signal peptide sequence of the bacterial pectate lyase; rbs: ribosome binding site which originates from the *E. coli* lacZ gene (lacZ), from the bacteriophage T7 gene 10 (T7g10) or from the *E. coli* skp gene (skp), -skp: gene which codes for the bacterial periplasmic factor Skp/OmpH; tHP: strong transcription terminator; tIPP: transcription terminator; $V_H$ and $V_L$: variable region of the heavy and light chains.
Figure 10:
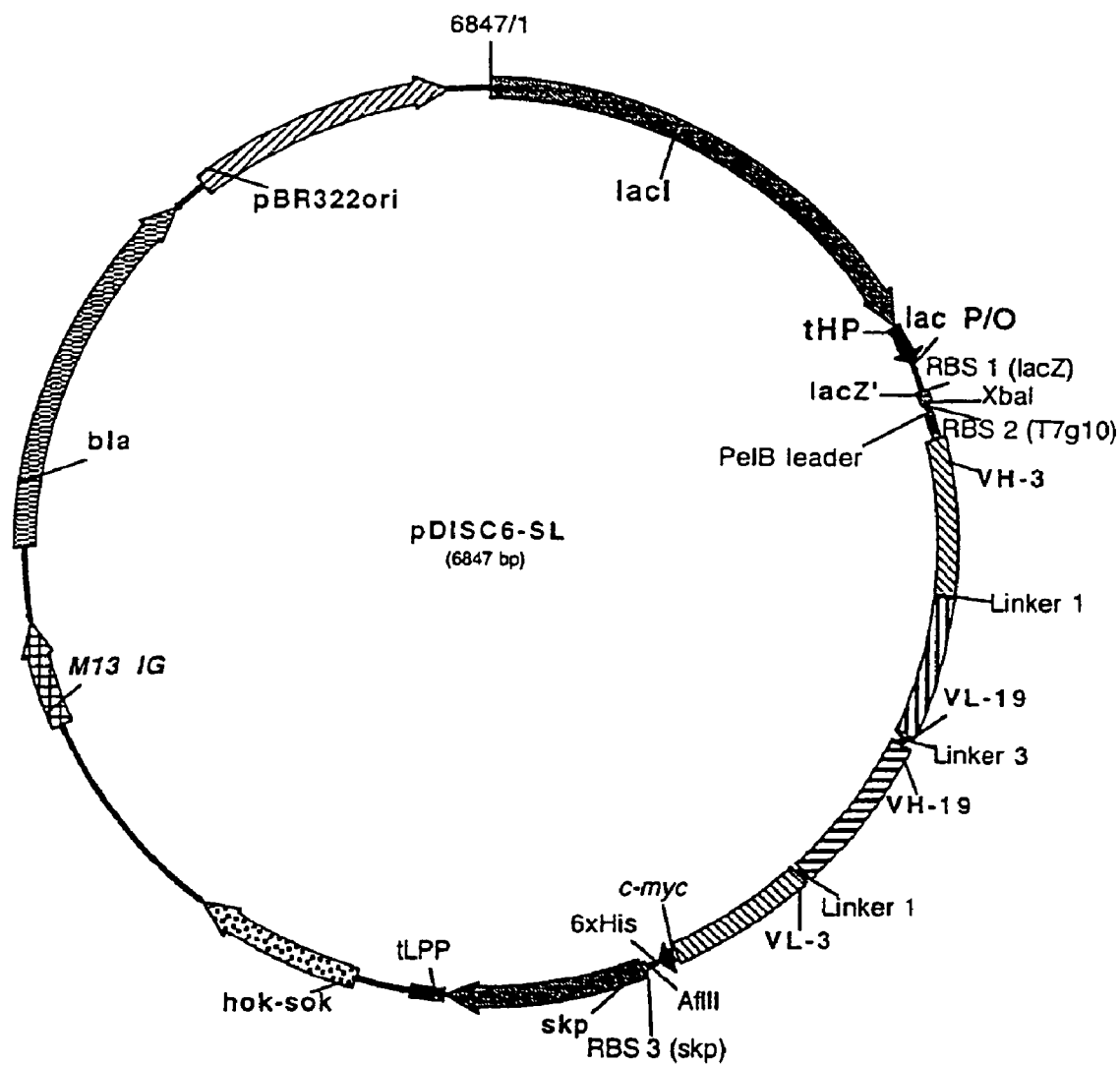
FIG. 10 shows a diagram of the expression plasmid pDISC6-SL. 6×His: sequence which codes for six C-terminal histidine residues; bla: gene which codes for β-lactamase responsible for ampicillin resistance; bp: base pairs: c-myc: sequence coding for an epitope which is recognized by the 9E10 antibody; hok-sok: plasmid-stabilized DNA locus; Lacd: gene which codes for the Lac represser; Lac P/O: wt lac-operon promoter/operator; LacZ': gene which codes for the α-peptide of β-galactosidase; linker 1: sequence which codes for a GlyGly dipeptide which links the $V_H$ and $V_L$ domains; linker 3: sequence which codes for a GlyGlyProGlySer oligopeptide linking the hybrid scFv fragments: M13 IG: intergenic region of the M13 bacteriophage; pBR322ori: origin of DNA replication; Pel-B leader: signal peptide sequence of the bacterial pectate lyase; rbs: ribosome binding site originating from the *E. coli* lacZ gene (lacZ), from the bacteriophage TV gene 10 (T7g10) or from the *E. coli* skp gene (skp); skp: gene which codes for the bacterial periplasmic factor Skp/OmpH; tHP: strong transcription terminator; tIPP: transcription terminator; $V_H$ and $V_L$: variable region of the heavy and light chains.

Construction of the Plasmids pDISC5-LL and pDISC5-SL for the Expression of Bivalent, Bispecific and/or Tetravalent, Bispecific F$_v$ Antibody Constructs in Bacteria by High Cell Density Fermentation Expression vectors were prepared which contained the hok/sok plasmid-free cell suicide system and a gene which codes for the Skp/OmpH periplasmic factor for a greater production of recombinant antibodies. The skp gene was amplified by PCR using the primers skp-1,5'-CGA ATT CTT AAG ATA AGA AGG AGT TTA TTG TGA AAA AGT GGT TAT TAG CTG CAG G (SEQ ID NO: 10) and skp-2,5'-CGA ATT AAG CTT CAT TAT TTA ACC TGT TTC AGT ACG TCG G (SEQ ID NO:11) using the plasmid pGAH317 (Hoick and Kleppe, 1988, Gene 67, 117-124). The resulting PCR fragment was cleaved by AflII and HindIII and inserted in the AflII/HindIII-linearized plasmid pHKK (Horn et al., 1996, Appl. Microbiol. Biotechnol. 46, 524-532) so as to obtain the vector pSKK. The genes obtained in the plasmids pDISC3x19-LL and pDISC3x19-SL and coding for the scFv antibody constructs were amplified by means of the primers fe-1,5'-CGA ATT TCT AGA TAA GAA GGA GAA ATT AAC CAT GAA ATA CC (SEQ ID NO:12) and fe-2,5'-CGA ATT CTT AAG CTA TTA GTG ATG GTG ATG GTG ATG TGA G (SEQ ID NO:13). The XbaI/AflII-cleaved PCR fragments were inserted in pSKK before the skp insert so as to obtain the expression plasmids pDISC5-LL and pDISC6-SL, respectively, which contain tri-cistronic operons under the control of the lac promoter/operator system (FIGS. 9, 10).

---

What is claimed is:

1. A bivalent monomeric $F_v$ antibody formed by one single-chain $F_v$ monomer having four variable domains, wherein said four variable domains are $V_H$-A, $V_L$-B, $V_H$-B and $V_L$-A, wherein $V_H$-A and $V_L$-A are $V_H$ and $V_L$ domains of an antibody specific for antigen A, respectively, and $V_H$-B and $V_L$-B are $V_H$ and $V_L$ domains of an antibody specific for antigen B, respectively; $V_H$-A is linked to $V_L$-B by peptide linker 1, $V_L$-B is linked to $V_H$-B by peptide linker 2 and $V_H$-B is linked to $V_L$-A by peptide linker 3; said peptide linker 1 and said peptide linker 3 are a peptide bond or have 1 to about 10 amino acids; and said peptide linker 2 has about 10 to about 30 amino acids; $V_H$-A and $V_L$-A associate intramolecularly to form a binding site for antigen A; and $V_L$-B and $V_H$-B associate intramolecularly to form a binding site for antigen B.

2. The $F_v$ antibody of claim 1, wherein said peptide linker has 2 have 11 to about 20 amino acids.

3. The $F_v$ antibody of claim 1, wherein said peptide linker has 2 have 15 to 20 amino acids.

4. The $F_v$ antibody of claim 1, wherein said peptide linker 2 is $(G_4S)_4$ (SEQ ID NO: 14).

5. The $F_v$ antibody of claim 1, wherein said peptide linker 1 and said peptide linker 3 have the amino acid sequence GG.

6. The $F_v$ antibody of claim 1, wherein said peptide linker 1 and said peptide linker 3 have the same amino acid sequence.

7. The $F_v$ antibody of claim 1, wherein said antibody is monospecific.

8. The $F_v$ antibody of claim 1, wherein said antibody is bispecific.

9. The $F_v$ antibody of claim 1, wherein said antibody is specific for an antigen selected from the group consisting of CD3 and CD19.

10. The $F_v$ antibody of claim 9, wherein said antibody is specific for CD3 and CD19.

11. A composition comprising said $F_v$ antibody of claim 1 for diagnosis and/or treatment of diseases.

* * * * *

```
                     SEQUENCE LISTING

<160> NUMBER OF SEQ ID NOS: 14

<210> SEQ ID NO 1
<211> LENGTH: 42
<212> TYPE: DNA
<213> ORGANISM: Artificial Sequence
<220> FEATURE:
<223> OTHER INFORMATION: Primer

<400> SEQUENCE: 1
tcacacagaa ttcttagatc tattaaagag gagaaattaa cc                 42

<210> SEQ ID NO 2
<211> LENGTH: 40
<212> TYPE: DNA
<213> ORGANISM: Artificial Sequence
<220> FEATURE:
<223> OTHER INFORMATION: Primer

<400> SEQUENCE: 2
agcacacgat atcaccgcca agcttgggtg ttgttttggc                    40

<210> SEQ ID NO 3
<211> LENGTH: 43
<212> TYPE: DNA
<213> ORGANISM: Artificial Sequence
<220> FEATURE:
<223> OTHER INFORMATION: Primer

<400> SEQUENCE: 3
agcacacaag cttggcggtg atatcttgct cacccaaact cca                43

<210> SEQ ID NO 4
<211> LENGTH: 57
<212> TYPE: DNA
<213> ORGANISM: Artificial Sequence
<220> FEATURE:
<223> OTHER INFORMATION: Primer

<400> SEQUENCE: 4
agcacactct agagacacac agatctttag tgatggtgat ggtgatgtga gtttagg  57
```

```
<210> SEQ ID NO 5
<211> LENGTH: 33
<212> TYPE: DNA
<213> ORGANISM: Artificial Sequence
<220> FEATURE:
<223> OTHER INFORMATION: Primer

<400> SEQUENCE: 5
cagccggcca tggcgcaggt gcaactgcag cag                           33

<210> SEQ ID NO 6
<211> LENGTH: 102
<212> TYPE: DNA
<213> ORGANISM: Artificial Sequence
<220> FEATURE:
<223> OTHER INFORMATION: Primer

<400> SEQUENCE: 6
tatatactgc agctgcacct ggctaccacc accaccggag ccgccaccac cgctaccacc    60
gccgccagaa ccaccaccac cagcggccgc agcatcagcc cg                      102

<210> SEQ ID NO 7
<211> LENGTH: 56
<212> TYPE: DNA
<213> ORGANISM: Artificial Sequence
<220> FEATURE:
<223> OTHER INFORMATION: Primer

<400> SEQUENCE: 7
tatatactgc agctgcacct gcgaccctgg gccaccagcg gccgcagcat cagccg        56

<210> SEQ ID NO 8
<211> LENGTH: 45
<212> TYPE: DNA
<213> ORGANISM: Artificial Sequence
<220> FEATURE:
<223> OTHER INFORMATION: Primer

<400> SEQUENCE: 8
ccgtgaattc caggtgcaac tgcagcagtc tggggctgaa ctggc                    45

<210> SEQ ID NO 9
<211> LENGTH: 34
<212> TYPE: DNA
<213> ORGANISM: Artificial Sequence
<220> FEATURE:
<223> OTHER INFORMATION: Primer

<400> SEQUENCE: 9
ggtcgacgtt aaccgacaaa caacagataa aacg                                34

<210> SEQ ID NO 10
<211> LENGTH: 55
<212> TYPE: DNA
<213> ORGANISM: Artificial Sequence
<220> FEATURE:
<223> OTHER INFORMATION: Primer

<400> SEQUENCE: 10
cgaattctta agataagaag gagtttattg tgaaaaagtg gttattagct gcagg         55

<210> SEQ ID NO 11
<211> LENGTH: 40
<212> TYPE: DNA
<213> ORGANISM: Artificial Sequence
<220> FEATURE:
```

```
<223> OTHER INFORMATION: Primer

<400> SEQUENCE: 11
cgaattaagc ttcattattt aacctgtttc agtacgtcgg                              40

<210> SEQ ID NO 12
<211> LENGTH: 41
<212> TYPE: DNA
<213> ORGANISM: Artificial Sequence
<220> FEATURE:
<223> OTHER INFORMATION: Primer

<400> SEQUENCE: 12
cgaatttcta gataagaagg agaaattaac catgaaatac c                            41

<210> SEQ ID NO 13
<211> LENGTH: 40
<212> TYPE: DNA
<213> ORGANISM: Artificial Sequence
<220> FEATURE:
<223> OTHER INFORMATION: Primer

<400> SEQUENCE: 13
cgaattctta agctattagt gatggtgatg gtgatgtgag                              40

<210> SEQ ID NO 14
<211> LENGTH: 20
<212> TYPE: PRT
<213> ORGANISM: Artificial Sequence
<220> FEATURE:
<223> OTHER INFORMATION: Linker Region from Construct

<400> SEQUENCE: 14

Gly Gly Gly Gly Ser Gly Gly Gly Gly Ser Gly Gly Gly Gly Ser Gly
1               5                   10                  15

Gly Gly Gly Ser
            20
```